(12) United States Patent
Patel et al.

(10) Patent No.: US 9,149,439 B2
(45) Date of Patent: Oct. 6, 2015

(54) MULTI-PARTICULATE, MODIFIED-RELEASE COMPOSITION

(75) Inventors: Ashish Anilbhai Patel, North Brunswick, NJ (US); Suresh Palaniswamy, East Windsor, NJ (US); Pablo Davila, East Windsor, NJ (US)

(73) Assignee: Sandoz AG (CH)

( * ) Notice: Subject to any disclaimer, the term of this patent is extended or adjusted under 35 U.S.C. 154(b) by 1354 days.

(21) Appl. No.: 11/085,671

(22) Filed: Mar. 21, 2005

(65) Prior Publication Data
US 2006/0210631 A1    Sep. 21, 2006

(51) Int. Cl.
*A61K 9/14*    (2006.01)
*A61K 9/50*    (2006.01)
*A61K 9/20*    (2006.01)
*A61K 31/606*    (2006.01)

(52) U.S. Cl.
CPC ............ *A61K 9/5073* (2013.01); *A61K 9/2081* (2013.01); *A61K 31/606* (2013.01)

(58) Field of Classification Search
None
See application file for complete search history.

(56) References Cited

U.S. PATENT DOCUMENTS

| | | | |
|---|---|---|---|
| 5,171,580 A | | 12/1992 | Iamartino et al. |
| 5,541,170 A | * | 7/1996 | Rhodes et al. ............... 514/166 |
| 5,541,171 A | * | 7/1996 | Rhodes et al. ............... 514/166 |
| 6,365,184 B1 | * | 4/2002 | Depui et al. .................. 424/469 |
| 6,733,789 B1 | * | 5/2004 | Stark et al. ................... 424/490 |
| 2001/0026808 A1 | | 10/2001 | Woolfe et al. |
| 2003/0035835 A1 | * | 2/2003 | Bartholomaeus et al. .... 424/468 |
| 2004/0224015 A1 | * | 11/2004 | Haldar et al. ................. 424/465 |
| 2005/0053660 A1 | | 3/2005 | Beckert et al. |
| 2005/0142187 A1 | * | 6/2005 | Treacy et al. ................. 424/451 |
| 2006/0003005 A1 | * | 1/2006 | Cao et al. ..................... 424/470 |
| 2006/0223787 A1 | * | 10/2006 | Devane et al. ................ 514/159 |

FOREIGN PATENT DOCUMENTS

| | | | |
|---|---|---|---|
| EP | 0 453 001 | | 10/1991 |
| EP | 0453001 | * | 10/1991 |
| IT | EP 0453001 A1 | * | 10/1991 |
| WO | WO 92/16206 | | 10/1992 |

\* cited by examiner

*Primary Examiner* — Snigdha Maewall
(74) *Attorney, Agent, or Firm* — Luedeka Neely Group, P.C.

(57) ABSTRACT

A multi-particulate, modified-release pharmaceutical composition for the oral administration of an active ingredient to the colon, wherein said particles comprise:

(a) a core comprising an active ingredient or a pharmaceutically acceptable salt or ester thereof, and optionally one or more excipients;

(b) a first coating applied to the surface of the core, wherein said first coating is insoluble in gastric juice and in intestinal juice below pH 7, but soluble in colonic intestinal juice; and (c) a second coating applied to the surface of the first coating.

24 Claims, No Drawings

MULTI-PARTICULATE, MODIFIED-RELEASE COMPOSITION

FIELD OF THE INVENTION

The present invention provides a multi-particulate, modified-release pharmaceutical composition for the oral administration of an active ingredient to the colon. The composition has particular, but not exclusive, application to the administration of 5-aminosalicylic acid (mesalamine) for the treatment of colonic or rectal disorders, such as ulcerative colitis.

BACKGROUND OF THE INVENTION

In the treatment of diseases or ailments of the colon or rectum administration of the pharmacologically active agent to the affected site may be required. Orally administrable pharmaceutical compositions however have frequently been found ineffective in this respect as a result of the absorption of the pharmacologically active agent in the digestive tract before the colon or rectum is reached. Consequently, the delivery of pharmacologically active agents to the colon or rectum has conventionally been achieved by rectal administration, by the use of either suppositories, aerosols, or enemas. However, rectal administration generally is less convenient and less acceptable to a patient than oral administration. Further, said rectal administration is not suitable for treating the right side of the colon. In particular, suppositories are only effective for the rectum and enemas rarely reach beyond the left side of the colon.

Several "delayed-release" forms of orally administrable pharmaceuticals have been proposed. UK Patent No. 1219026 describes to a method to embed individual particles of a pharmacologically active agent in a slowly-disintegrating or slowly-dissolving resin having a particular dissolution profile to provide an orally administrable pharmaceutical composition for selectively administering the agent to the large intestine. The resin is selected such that the agent remains substantially protected by the resin while the particles travel through the stomach and small intestines of a patient and that the agent is substantially completely exposed at the time the particles reach the large intestine.

UK Patent No. 2021409 describes sustained or controlled release compositions containing 5-aminosalicylic acid in the form of particles or granules which are coated with a slowly soluble or digestible or semi-permeable layer of material, such as beeswax, carnauba wax, stearic or palmitic acids or cetyl alcohol. Reference also is made to coating tablets of the coated or uncoated 5-aminosalicylic acid with a continuous film of a material, such as shellac or cellulose acetate phthalate, which is resistant and impermeable to gastric secretions but susceptible to intestinal secretions.

International Patent Application WO 81/02671 describes sustained-release tablets prepared from granules containing 5-aminosalicylic acid which are coated with a cellulose derivative, such as ethyl cellulose.

European Patent Application No. 40590A describes a method for coating a core of 5-aminosalicylic acid with a coating material comprising at least: (a) 10-85% by weight of an anionic carboxylic polymer soluble only above pH 5.5; and (b) 15-90% by weight of a water-soluble, quaternary ammonium substituted acrylic polymer. It is stated that the coating normally will be 3-60 microns, preferably 10-30 microns thick and that partly methyl esterified methacrylic acid polymers are suitable anionic carboxylic polymers for use as component (a). In the Examples, Eudragit® L and a mixture of Eudragit® L and Eudragit® S constitute the component (a) and in all cases the coatings dissolved at below pH 7.

U.S. Pat. No. 5,541,170 describes an orally administrable pharmaceutical composition for selectively administering 5-aminosalicylic acid, or pharmaceutically acceptable salt or ester thereof, to the large intestine, comprising a solid oral dosage form containing a pharmaceutically effective amount for the treatment of ulcerative colitis or Crohn's disease of the colon of said 5-aminosalicylic acid, salt or ester, said solid oral dosage form being coated with a layer which is insoluble in gastric juice and in intestinal juice below pH 7, but soluble in colonic intestinal juice, whereby the dosage form releases the 5-aminosalicylic acid, salt or ester to the right side of the colon.

U.S. Pat. No. 5,541,171 describes a non-sustained release orally administrable pharmaceutical composition for selectively administering 5-aminosalicylic acid or a pharmaceutically acceptable salt or ester thereof to the large intestine, the composition comprising a solid oral dosage form containing a pharmaceutically effective amount for the treatment of ulcerative colitis or Crohn's disease of said 5-aminosalicylic acid, ester or salt and said oral dosage form is coated with a 60-150 micron thick layer of an anionic co-polymer of methacrylic acid and methacrylic acid methyl ester in which the ratio of free carboxyl groups to ester groups is about 1:2 and which is insoluble in gastric juice and in intestinal juice below pH 7, but soluble in colonic intestinal juice, whereby the oral dosage form remains intact until it reaches the colon and releases 5-aminosalicylic acid to the right side of the colon.

SUMMARY OF THE INVENTION

The invention provides a multi-particulate, modified-release pharmaceutical composition for the oral administration of an active ingredient to the colon, wherein said particles comprise:
  (a) a core comprising an active ingredient or a pharmaceutically acceptable salt or ester thereof, and optionally one or more excipients;
  (b) a first coating applied to the surface of the core, wherein said first coating is insoluble in gastric juice and in intestinal juice below pH 7, but soluble in colonic intestinal juice; and
  (c) a second coating applied to the surface of the first coating.

According to another aspect, the invention provides a multi-particulate, modified-release pharmaceutical composition in the form of a tablet for delivering 5-aminosalicylic acid, salt or ester thereof, to the right side of the colon, wherein said particles comprise:
  (a) a core comprising 5-aminosalicylic acid, or a pharmaceutically acceptable salt or ester thereof, and optionally one or more excipients;
  (b) a first coating applied to the surface of the core, wherein said first coating is insoluble in gastric juice and in intestinal juice below pH 7, but soluble in colonic intestinal juice; and
  (c) a second coating applied to the surface of the first coating,
wherein said tablet is coated with an enteric coating which is insoluble in gastric juice and soluble in intestinal juice at a pH >5. In a preferred embodiment, the particles individually do not contain a therapeutically effective amount of 5-aminosalicylic acid.

The multi-particulate, modified-release pharmaceutical composition of the invention is particularly useful for the administration of active ingredients, especially topically active agents, to the colon, preferably the right side, which cannot reliably be reached with a rectally administered dosage form.

DESCRIPTION OF THE INVENTION

The invention provides a multi-particulate, modified-release pharmaceutical composition for the oral administration of an active ingredient to the colon, wherein said particles comprise:
(a) a core comprising an active ingredient or a pharmaceutically acceptable salt or ester thereof, and optionally one or more excipients;
(b) a first coating applied to the surface of the core, wherein said first coating is insoluble in gastric juice and in intestinal juice below pH 7, but soluble in colonic intestinal juice; and
(c) a second coating applied to the surface of the first coating.

As used herein, "particles" includes pellets, granules and the like. The particles can be of any shape, such as, e.g., spheroids or ellipsoids, or may be irregularly shaped. As used herein, "polymer" includes polymers, co-polymers, ter-polymers and the like.

As active ingredients in the composition of the invention, those compounds conventionally used in the treatment of colitis, ulcerative colitis, Crohn's disease, idiopathic protitis and other diseases or disorders of the colon or rectum are of particular interest. Examples of active ingredients include, but are not limited to, non-steroidal anti-inflammatory compounds, steroids, compounds active in the relief of constipation or diarrhea, compounds active in the relief of spasm and in the improvement of motility, carminative essential oils, compounds for removal of excessive bile acids, anti-bacterial or anti-parasitic compounds, anti-ulcer agents, anti-fungal agents, analgesic agents, antibiotics, anti-cancer agents, anesthetics, anti-infectives, laxatives and anti-obesity agents. A mixture of active ingredients may also be used.

Specific examples of active ingredients include, but are not limited to, acetylcysteine, acetaminophen, acetylsalicylic acid, acyclovir, aminoacetic acid, 5-aminosalicylic acid, amoxicillin, ampicillin, azithromycin, beclomethasone, beclomethasone dipropionate, beclomethasone valerate, benzocaine, betamethasone, budesonide, cefachlor, cefalexin, cefatroxil, cefazolin, cefixime, cefotaxime, ceftazidime, ceftriaxone, cefuroxime, chlorhexidine, chloroguine, cholestyramine, cyclosporin, ciprofloxacin, clarithromycin, clavulanic acid, clotrimazole, codeine, desogestrel, dexamethasone, dextropropoxiphen, diclofenac, dihydrocodeine, disodohydroxyquin, erythromycin, famotidine, fentanyl, fluconazole, flurbiprofen, gentamicin, hydrocodone, hydrocortisone, hydromorphone, ibuprofen, indomethacin, iodochlorhydroxyquin, ketotifen, ketoconazole, ketoprofen, ketorolac, lactulose, loperamide, methylprednisolone, miconazole, morphine, naproxen, neomycin, nimodipine, norfloxacin, ofloxacin, penicillin G, penicillin V, peppermint oil, piroxicam, polymyxin B, prednisolone, prednisone, prednisolone phosphate, prednisolone metasulpho-benzoate sodium, prednisolone sodium phosphate, salicylates, salicylic acid, sulbactam, sulfasalazine, tetracyclines, and pharmaceutically acceptable salts or esters thereof. The active ingredient is preferably selected from 5-aminosalicylic acid, pregnisolone, indomethacin and ibuprofen.

In addition to the active ingredient, the core may optionally contain one or more pharmaceutically acceptable excipients. Examples of such excipients are carriers, binders, diluents, plasticizers, anti-caking agents, fillers, solubilizing agents, disintegrants, lubricants, surfactants, stabilizers, anti-oxidants, anti-adherents, preservatives, glidants and pigments. A combination of excipients may also be used. Such excipients are known to those skilled in the art.

The amount of active ingredient in the core of the compositions of the invention may vary from 0.1-100 weight percent (wt. %), based on the total weight of the core. Preferably the active ingredient is present in an amount of from 0.1-99 wt. %, preferably from 20-90 wt. %, more preferably 30-80 wt. %, based on the total weight of the core.

The core of the particles of the invention is preferably prepared by mixing at least one active ingredient, and optionally one or more excipients, in the presence or absence of a solvent, to form a premix. The premix is preferably in the form of a solid dispersion or a homogeneous suspension. The premix is preferably subject to high-shear granulation, extrusion, spheronization or wet granulation, to form particles. More preferably, the premix is subject to extrusion. The extrudate are shaped into particles of various shapes and sizes by spheronization. The particles are preferably dried and screened to obtain particles of the desired sizes.

Drying techniques useful for drying the particles include spray-drying, fluid bed drying, flash drying, ring drying, micron drying, tray drying, vacuum drying, radio-frequency drying and microwave drying. A preferred drying technique is tray drying.

The particles of the desired size may be obtained by sieving/sizing techniques which are known to those skilled in the art. Preferred sifters are Sweco LS24 or equivalent vibrating sifters preferably equipped with U.S. Standard No. 10-60 sieves.

The first coating, which is applied to the surface of the core particles, is insoluble in gastric juice and in intestinal juice below pH 7, but soluble in colonic intestinal juice. The first coating preferably dissolves in colonic intestinal juice at a pH above pH 7.0. A preferred first coating comprises an anionic polymer. The anionic polymer preferably contains anionic groups which are selected from free carboxyl groups and esterified carboxyl groups. The anionic polymer is preferably a polymer prepared by polymerizing methacrylic acid or acrylic acid and a methacrylic acid or acrylic acid alkyl ester, wherein the alkyl group has from 1-6 carbon atoms. More preferably, the anionic polymer is a polymer of methacrylic acid and methacrylic acid methyl ester. More preferably, the polymer of methacrylic acid and methacrylic acid methyl ester has a ratio of free carboxyl groups to ester groups of about 1:2 or 1:1. A preferred anionic polymer is available under the trademark "Eudragit® S100" from Rohm Pharma.

In one embodiment of the invention, the first coating additionally comprises an alkali agent. While not wishing to be bound by any particular theory, the present inventors believe that the alkali agent form a latex dispersion with the first coating polymer which maintains homogeneity of a first coating dispersion. Suitable alkali agents include, but are not limited to, the inorganic salts of metals of Groups I and II of the Periodic Table. Thus, salts of alkali and alkaline earth metals are operable. The anionic portion of the salt may be any which does not deleteriously affect the adhesive properties of the first coating. Thus, borates, silicates and carbonates are contemplated. Specific examples of alkali agents include ammonia, ammonium hydroxide, sodium chloride, calcium hydroxide, lithium hydroxide, magnesium hydroxide, potassium hydroxide, barium hydroxide, sodium hydroxide, calcium carbonate, lithium carbonate, magnesium carbonate, potassium carbonate, sodium carbonate, calcium hydrogencarbonate, lithium hydrogencarbonate, magnesium hydrogencarbonate, potassium hydrogencarbonate and sodium hydrogencarbonate. A preferred alkali agent is ammonium hydroxide. A mixture of alkali agents may also be used.

The amount of alkali agent is preferably from about 1 wt. % to about 90 wt. %, based on the total weight of the dry polymer, commonly referred to as "total solids". More preferably, the amount of alkali is from about 10 wt. % to about 80 wt. % of total solids, and most preferably about 40 wt. %.

In one embodiment of the invention, the first coating additionally comprises a plasticizer. The plasticizer is preferably selected from acetyl-triethyl citrate, acetyl tributyl-, tributyl-, triethyl-citrate, glycerol diacetate, glycerol triacetate, acetylated monoglycerides, castor oil, dibutyl-phthalate, diamyl-phthalate, diethyl-phthalate, dimethyl-phthalate, dipropyl-phthalate, di-(2-methoxy- or 2-ethoxyethyl)-phthalate, ethylphthalyl glycolate, butylphthalylethyl glycolate, butylglycolate, propylene glycol, polyethylene glycol, diethyladipate, di-(2-methoxy- or 2-ethoxyethyl)-adipate, benzophenone, diethyl- and diburylsebacate, dibutylsuccinate, dibutyltartrate, diethylene glycol dipropionate, ethyleneglycol diacetate, ethyleneglycol dibutyrate, ethyleneglycol dipropionate, tributyl phosphate, tributyrin, polyethylene glycol (PEG) sorbitan monooleate and sorbitan monooleate. More preferably, the plasticizer used in the enteric coating is a citric acid ester, such as triethyl citrate. A mixture of plasticizers may also be used.

The amount of plasticizer to be used in the first coating is preferably from about 50% to about 100%, more preferably from about 60% to about 80%, and most preferably about 70%, based on the weight of the dry polymer, i.e., total solids.

The first coating is applied to the surface of the core. The coating thickness should be sufficient to ensure that the oral dosage form remains intact until it reaches the colon. Thus, the amount of the first coating is preferably from about 1 wt. % to about 30 wt. %, based on the total weight of the coated particles. More preferably, the amount of the first coating is from about 7 wt. % to about 20 wt. %, most preferably from about 12 wt. % to about 17 wt. %, based on the total weight of the first coating and core.

A sealant may optionally be applied to the surface of the core, prior to application of the first coating. A sealant provides a physical barrier between the active ingredient and the first coating, to minimize or prevent interaction between the active ingredient and the coating. Examples of sealants include, but are not limited to, hydroxypropyl methylcellulose, hydroxypropylethylcellulose, hydroxypropyl propylcellulose, hydroxypropylbutylcellulose, cellulose acetate methyl carbamate, cellulose acetate diethyl aminoacetate, semi-permeable polyurethanes, semi-permeable sulfonated polystyrenes and semi-permeable cross-linked polymers, such as poly(vinylbenzyltrimethyl)ammonium chloride. A preferred sealant is hydroxypropylmethylcellulose.

The first coating can be deposited on the surface of the core by any method known to those skilled in the art, such as spray coating, spray congealing techniques. Spraying can be carried out by pan coating or by use of a fluid bed equipped with a Wurster column.

Following deposition of the optional sealant and the first coating, the particles coated with the first coating are cured. "Curing" means that the coated particles are held at a controlled temperature for a sufficient period of time to provide stable release rates. Stability in release rate is indicated when further curing does not affect the release rate. In contrast, instability of release rate means that as the cure time is increased, the release rate continues to vary. Curing for a sufficient time ensures that substantially the same release rate is obtained with all particles of a particular size range coated with a given amount of a given coating composition. A suitable curing time can be determined by one of skill in the art without undue experimentation, by noting the variability in in vitro release times as curing time is varied.

Curing can be accomplished, e.g., in a fluid bed, static bed, or a forced air oven. Curing can be carried out at any temperature preferably above room temperature, "room temperature" being defined as from about 18° C. to about 25° C. Preferably, curing is carried out at a temperature of from about 25° C. to about 40° C., more preferably from about 27° C. to about 35° C., and most preferably about 30° C. Curing time can range from several minutes to several hours. Preferably, the coated particles are cured for at least about 30 minutes.

A second coating is applied to the surface of the first coating. The second coating is preferably selected from cross-linked polyvinyl pyrrolidone; non-cross-linked polyvinylpyrrolidone; hydroxypropylmethyl cellulose phthalate; hydroxypropylmethyl cellulose acetate succinate; cellulose acetate succinate; cellulose acetate phthalate; hydroxypropylmethyl cellulose acetate succinate; cellulose acetate trimellitate; hydroxypropyl methyl cellulose phthalate; hydroxypropyl methyl cellulose acetate succinate; starch acetate phthalate; polyvinyl acetate phthalate; carboxymethyl cellulose; methyl cellulose phthalate; methyl cellulose succinate; methyl cellulose phthalate succinate; methyl cellulose phthalic acid half ester; ethyl cellulose succinate; carboxymethylamide; potassium methacrylatedivinylbenzene co-polymer; polyvinylalcohols; co-polymers of acrylic acid and/or methacrylic acid with at least one monomer selected from the group consisting of methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate and octadecyl acrylate; polyvinyl acetate; fats; oils; waxes; fatty alcohols; shellac; gluten; ethylacrylate-maleic acid anhydride co-polymer; maleic acid anhydride-vinyl methyl ether co-polymer; styrol-maleic acid co-polymer; 2-ethyl-hexyl-acrylate maleic acid anhydride; crotonic acid-vinyl acetate co-polymer; glutaminic acid/glutamic acid ester co-polymer; carboxymethylethylcellulose glycerol monooctanoate; polyarginine; poly(ethylene); poly(propylene); poly(ethylene oxide); poly(ethylene terephthalate); poly(vinyl isobutyl ether); poly(vinyl chloride); polyurethane; polyvinyl/maleic anhydride co-polymers; poly(methacrylic acid); ethylene/maleic anhydride co-polymers and ammonio methacrylate co-polymers. Ammonio methacrylate co-polymers comprise acrylic and/or methacrylic ester groups together with quaternary ammonium groups. A mixture of second coatings may also be used. More preferably, the second coating is a mixture of polyvinylpyrrolidone and hydroxypropylmethylcellulose.

In one embodiment of the invention, the second coating additionally comprises a plasticizer. The plasticizer is preferably selected from acetyl-triethyl citrate, acetyl tributyl-, tributyl-, triethyl-citrate, glycerol diacetate, glycerol triacetate, acetylated monoglycerides, castor oil, dibutyl-phthalate, diamyl-phthalate, diethyl-phthalate, dimethyl-phthalate, dipropyl-phthalate, di-(2-methoxy- or 2-ethoxyethyl)-phthalate, ethylphthalyl glycolate, butylphthalylethyl glycolate, butylglycolate, propylene glycol, polyethylene glycol, diethyladipate, di-(2-methoxy- or 2-ethoxyethyl)-adipate, benzophenone, diethyl- and diburylsebacate, dibutylsuccinate, dibutyltartrate, diethylene glycol dipropionate, ethyleneglycol diacetate, ethyleneglycol dibutyrate, ethyleneglycol dipropionate, tributyl phosphate, tributyrin, PEG sorbitan monooleate and sorbitan monooleate. More preferably, the plasticizer used in the second coating is polyethylene glycol. A mixture of plasticizers may also be used.

The amount of plasticizer to be used in the second coating is preferably from about 50% to about 100%, more preferably from about 70% to about 90%, and most preferably about 80%, based on the weight of the total solids in the second coating.

The second coating is applied to the surface of the first coating on the particles. The amount of the second coating is preferably from about 1 wt. % to about 70 wt. %, based on the total weight of the first coated particles. More preferably, the amount of the second coating is from about 10 wt. % to about 50 wt. %, most preferably from about 20 wt. % to about 30 wt. %, based on the total weight of the first coated particles.

The amount of the second coating should be sufficient to minimize damage, such as rupture, cracking, fissures, etc. to the surface of the first coating on the particles, especially during compression of the coated particles to form tablets. Damage to the first coating is highly undesirable because partially uncoated cores may result in unwanted variability in release rates of the active ingredient.

The second coating can be deposited on the surface of the first coating by any method known to those skilled in the art, such as spray application. Spraying can be carried out by pan coating or by use of a fluid bed equipped with a Wurster column.

Following deposition of the second coating, the particles coated with the second coating may be cured. Curing can be accomplished, e.g., in a fluid bed or a forced air oven. Curing can be carried out at any temperature preferably above room temperature, "room temperature" being defined as from about 18° C. to about 25° C. Preferably, curing is carried out at a temperature of from about 30° C. to about 70° C., more preferably from about 40° C. to about 60° C., and most preferably about 50° C. Curing time can range from several minutes to several hours. Preferably, the coated particles are cured for at least about 30 minutes.

The enteric coating, which is applied to the surface of the tablet, is insoluble in gastric juice and soluble in intestinal juice at a pH >5. The enteric coating is preferably selected from cross-linked polyvinyl pyrrolidone; non-cross-linked polyvinylpyrrolidone; hydroxypropylmethyl cellulose phthalate; hydroxypropylmethyl cellulose acetate succinate; cellulose acetate succinate; cellulose acetate phthalate; hydroxypropylmethyl cellulose acetate succinate; cellulose acetate trimellitate; hydroxypropyl methyl cellulose phthalate; hydroxypropyl methyl cellulose acetate succinate; starch acetate phthalate; polyvinyl acetate phthalate; carboxymethyl cellulose; methyl cellulose phthalate; methyl cellulose succinate; methyl cellulose phthalate succinate; methyl cellulose phthalic acid half ester; ethyl cellulose succinate; carboxymethylamide; potassium methacrylatedivinylbenzene co-polymer; polyvinylalcohols; co-polymers of acrylic acid and/or methacrylic acid with at least one monomer selected from the group consisting of methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate and octadecyl acrylate; polyvinyl acetate; fats; oils; waxes; fatty alcohols; shellac; gluten; ethylacrylate-maleic acid anhydride co-polymer; maleic acid anhydride-vinyl methyl ether co-polymer; styrol-maleic acid co-polymer; 2-ethyl-hexyl-acrylate maleic acid anhydride; crotonic acid-vinyl acetate co-polymer; glutaminic acid/glutamic acid ester co-polymer; carboxymethylethylcellulose glycerol monooctanoate; polyarginine; poly(ethylene); poly(propylene); poly(ethylene oxide); poly(ethylene terephthalate); poly(vinyl isobutyl ether); poly(vinyl chloride); polyurethane; polyvinyl/maleic anhydride co-polymers; poly(methacrylic acid); ethylene/maleic anhydride co-polymers; and ammonio methacrylate co-polymers. Ammonio methacrylate co-polymers comprise acrylic and/or methacrylic ester groups together with quaternary ammonium groups. More preferably, the enteric coating is a polymer of methacrylic acid and an acrylic or methacrylic ester, such as methylacrylate. A mixture of enteric coatings may also be used.

In one embodiment of the invention, the enteric coating additionally comprises a plasticizer. The plasticizer is preferably selected from acetyl-triethyl citrate, acetyl tributyl-, tributyl-, triethyl-citrate, glycerol diacetate, glycerol triacetate, acetylated monoglycerides, castor oil, dibutyl-phthalate, diamyl-phthalate, diethyl-phthalate, dimethyl-phthalate, dipropyl-phthalate, di-(2-methoxy- or 2-ethoxyethyl)-phthalate, ethylphthalyl glycolate, butylphthalylethyl glycolate, butylglycolate, propylene glycol, polyethylene glycol, diethyladipate, di-(2-methoxy- or 2-ethoxyethyl)-adipate, benzophenone, diethyl- and diburylsebacate, dibutylsuccinate, dibutyltartrate, diethylene glycol dipropionate, ethyleneglycol diacetate, ethyleneglycol dibutyrate, ethyleneglycol dipropionate, tributyl phosphate, tributyrin, PEG sorbitan monooleate and sorbitan monooleate. More preferably, the plasticizer used in the enteric coating is a citric acid ester, such as triethyl citrate. A mixture of plasticizers may also be used.

The amount of plasticizer to be used in the enteric coating is preferably from about 50% to about 100%, more preferably from about 70% to about 90%, and most preferably about 79%, based on the weight of the dry polymer, i.e., total solids.

In one embodiment of the invention, the enteric coating additionally comprises a filler. The filler is preferably in powder form and is preferably hydrophobic. Exemplary fillers include talc, colloidal silica, fumed silica, gypsum and glycerin monostearate. Talc is a particularly preferred filler.

The enteric coating is applied to the surface of the tablet. The amount of the enteric coating is preferably from about 1 wt. % to about 30 wt. %, based on the total weight of the uncoated tablet. More preferably, the amount of the enteric coating is from about 3 wt. % to about 20 wt. %, most preferably from about 5 wt. % to about 10 wt. %, based on the total weight of the uncoated tablet.

A solid dosage form comprising the coated particles can be prepared by methods known to those skilled in the art. For example, the coated particles may be compressed into tablets or filled into capsules.

In one embodiment of the invention, the multi-particulate, modified-release pharmaceutical composition is in the form of a tablet for delivering 5-aminosalicylic acid, salt or ester thereof, to the colon, preferably to the right side of the colon, wherein said particles comprise:
  (a) a core comprising 5-aminosalicylic acid, or a pharmaceutically acceptable salt or ester thereof, and optionally one or more excipients;
  (b) a first coating applied to the surface of the core, wherein said first coating is insoluble in gastric juice and in intestinal juice below pH 7, but soluble in colonic intestinal juice; and
  (c) a second coating applied to the surface of the first coating,
wherein said tablet is coated with an enteric coating which is insoluble in gastric juice and soluble in intestinal juice at a pH >5. Preferably, the particles individually do not contain a therapeutically effective amount of 5-aminosalicylic acid, or a pharmaceutically acceptable salt or ester thereof.

As noted above, it is within the scope of the invention for the multi-particulate, modified-release pharmaceutical compositions of the invention to include one or more pharmaceutically acceptable excipients. Examples of such excipients are binders, diluents, anti-caking agents, fillers, disintegrants, lubricants, surfactants, stabilizers, anti-oxidants, anti-adherents and glidants. A combination of excipients may also be used. Such excipients are known to those skilled in the art, and thus, only a limited number will be specifically referenced.

Examples of fillers include microcrystalline cellulose, starch, pregelatinized starch, modified starch(es), dibasic calcium phosphate dihydrate, calcium sulfate trihydrate, calcium sulfate dihydrate, calcium carbonate, lactose, dextrose, sucrose, mannitol and sorbitol. A combination of fillers may also be used. A preferred filler is a mixture of lactose monohydrate and microcrystalline cellulose.

Examples of lubricants include magnesium stearate, calcium stearate, zinc stearate, talc, propylene glycol, PEG, stearic acid, vegetable oil, sodium benzoate, sodium lauryl sulfate, magnesium lauryl sulfate, mineral oil and polyoxyethylene monostearate. A combination of lubricants may also be used.

Examples of binders include starches, e.g., potato starch, wheat starch, corn starch; gums, such as gum tragacanth, acacia gum and gelatin; microcrystalline cellulose, e.g., products known under the registered trademarks Avicel, Filtrak, Heweten or Pharmacel, hydroxypropyl cellulose, hydroxyethyl cellulose and hydroxypropylmethyl cellulose; and polyvinyl pyrrolidone, e.g., Kollidon VA-64 (copolymer of polyvinyl pyrrolidone and vinyl acetate, available from BASF).

Examples of glidants include colloidal silica, magnesium trisilicate, powdered cellulose, starch, talc, acetyl tributyl citrate, and tribasic calcium phosphate. Preferred glidants are silicon dioxide, low micron talc, colloidal silica, and acetyl tributyl citrate.

Examples of disintegrants include:
(i) natural starches, such as maize starch, potato starch and the like, directly compressible starches, e.g., Sta-rx® 1500; modified starches, e.g., carboxymethyl starches and sodium starch glycolate, available as Primojel®, Explotab®, Explosol®; and starch derivatives, such as amylose;
(ii) cross-linked polyvinylpyrrolidones, e.g., crospovidones, such as Polyplasdoneo XL and Kollidon® CL;
(iii) alginic acid and sodium alginate;
(iv) methacrylic acid-divinylbenzene co-polymer salts, e.g., Amberlite® IRP-88; and
(v) cross-linked sodium carboxymethylcellulose, available as, e.g., Ac-di-sol®, Primellose®, Pharmacel® XL, Explocel® and Nymcel® ZSX.

Additional disintegrants also include hydroxypropyl cellulose, hydroxypropylmethyl cellulose, croscarmellose sodium, sodium starch glycolate, polacrillin potassium, polyacrylates, such as Carbopol®, magnesium aluminium silicate and bentonite. A preferred disintegrant is croscarmellose sodium.

The following non-limiting examples illustrate further aspects of the invention.

EXAMPLE 1

Preparation of Core Particles.

| Ingredient | Formulation A (mg/tablet) | Formulation B (mg/tablet) | Formulation C (mg/tablet) | Formulation D (mg/tablet) |
|---|---|---|---|---|
| Mesalamine USP | 400 | 400 | 400 | 400 |
| Microcrystalline Cellulose NF | 50 | 39 | 39 | 37.5 |
| Lactose NF | 28.0 | 39.0 | 39.0 | 39.0 |
| Croscarmellose Sodium NF | 0.0 | 0.0 | 2.0 | 2.0 |
| Copolyvidone NF | 20.0 | 20.0 | 20.0 | 20.0 |
| Acetyl Tributyl Citrate NF | 2.0 | 2.0 | 0.0 | 0.0 |
| Colloidal Silicone Dioxide NF | 0.0 | 0.0 | 0.0 | 1.5 |
| Water USP | q.s. | q.s. | q.s. | q.s. |
| Total Weight | 500.0 | 500.0 | 500.0 | 500.0 |

The mesalamine, lactose, microcrystalline cellulose, and optionally croscarmellose sodium are mixed together in a 2.5 L high-shear VG5 Glatt granulator for about 5 minutes with an impeller set at 350 rpm and chopper set at 2,000 rpm, to form a premix. Separately, the co-polyvidone and optionally acetyl tributyl citrate are homogenized with water at room temperature until dissolved. A solution of the co-polyvidone and optionally acetyl tributyl citrate is sprayed on the premix to form a wet granulation. Optionally, colloidal silicone dioxide is sprinkled over the wet granulation and mixed until a uniform mixture is obtained. The resulting wet granulation is extruded through a 0.7 mm screen using a Nica E-140 extruder. The extrudate is spheronized using a Nica S-450 Spheronizer. The resulting spheroids or particles are discharged and placed on a tray which is placed in an oven at 60° C. for approximately 10 hours to obtain dried spheroids or particles. The dried spheroids or particles are screened using Sweco LS24 Mechanical Screen equipped with U.S. Standard Sieve No. 20 on the top and U.S. Standard Sieve No. 40 on the bottom. The mesalamine particles retained on Sieve No. 40 are collected.

EXAMPLE 2

First Coating Applied to Core Particles Prepared as Formulation D in Example 1.

| Ingredient | mg/Tablet |
|---|---|
| Mesalamine Particles | 500.0 |
| Methacrylic Acid NF (Eudragit ® S 100) | 35.0 |
| *1.7% NH$_3$ Solution | 17.8 |
| Triethyl Citrate NF | 24.5 |
| Lomicron Talc NF | 16.6 |
| **Water USP | q.s. |
| Total Weight | 576.1 |

*Ammonia forms a latex with methacrylic acid.
**Water is removed during processing.

Eudragit® S 100 is dispersed in ⅓ portion of water using a low-shear cross bar stirrer and a moderate speed. The Eudragit® S 100 dispersion is partially neutralized with 1 N ammonia solution forming an aqueous latex dispersion and mixed for 60 minutes. Triethyl citrate is added to the latex dispersion and mixed for 90 minutes. Lomicron talc is dispersed in ⅓ portion of water using a Silverson Mixer, and then poured into the latex dispersion. The remaining ⅓ portion of water is added to the dispersion and mixed until a uniform dispersion is obtained. The resulting dispersion is screened through U.S. Standard Sieve No. 60 to ensure the absence of agglomerates. The uniform dispersion is sprayed onto the mesalamine particles prepared in Example 1 using a Glatt GPCG 60 Fluid Bed Coater with 18-inch Wurster insert. The particles are coated until a desired weight gain is obtained forming delayed-release mesalamine particles. Upon completion of spraying, the coated particles are cured in the fluid bed for 30 minutes at a temperature of 30° C. The cured particles are screened using Sweco LS24 Mechanical Screen equipped with U.S. Standard Sieve No. 20 on the top and U.S. Standard Sieve No. 40 on the bottom. The first coated particles retained on Sieve No. 40 are collected.

EXAMPLE 3

| Second Coating Applied to First Coated Particles. | |
| --- | --- |
| Ingredient | mg/Tablet |
| Mesalamine Coated Particles From Ex. 2 | 576.10 |
| PEG 8000 NF | 135.64 |
| Hydroxypropylmethyl Cellulose (Pharmacoat 606) USP | 25.9 |
| Red Iron Oxide NF | 0.86 |
| Povidone K30 USP | 8.6 |
| Silicon Dioxide NF (Syloid 244 FP) | 1.8 |
| Water USP | q.s. |
| Total Weight | 748.9 |

Silicon dioxide, Red iron oxide, PEG 8000, Pharmacoat 606, and Povidone are mixed together until a homogenous dispersion is obtained. The uniform dispersion is sprayed onto the mesalamine first coated particles prepared in Example 2 using a Glatt GPCG 60 Fluid Bed Coater with 18-inch Wurster insert. The particles are coated until a desired weight gain is obtained. Upon completion of spraying, the coated particles are cured in the fluid bed for 30 minutes at a temperature of 40-70° C. The cured particles are screened using Sweco LS24 Mechanical Screen equipped with U.S. Standard Sieve No. 20 on the top and U.S. Standard Sieve No. 40 on the bottom. The second coated particles retained on Sieve No. 40 are collected.

EXAMPLE 4

| Preparation of a Tablet. | |
| --- | --- |
| Ingredient | mg/Tablet |
| Mesalamine Coated Particles from Ex. 3 | 748.90 |
| Croscarmellose Sodium NF | 15.0 |
| Lomicron Talc NF | 0.61 |
| Silicon Dioxide NF (Syloid 244 FP) | 5.49 |
| Total Weight (Core Tablet Compressed) | 770.0 |

The second coated particles from Example 3 are blended with croscarmellose sodium using a Bohle blender. Lomicron talc and Silicon dioxide are added through U.S. Sieve No. 20 to the blender and blending is continued to obtain a final mix. The final mix is compressed into tablets using a tablet press equipped with 0.2780"×0.6250" Modified Capsule Shaped Tooling. The amount of force used in the compression is enough to hold particles together without resulting in breaking of the coated particles or at least minimizing any breaking of the particles, and achieve a friability of <1% to obtain uncoated tablets.

EXAMPLE 5

| Applying a Enteric Coating to the Uncoated Tablets Formed in Example 4. | |
| --- | --- |
| Ingredient | mg/Tablet |
| Mesalamine Tablet from Ex. 4 | 770 |
| Acryl EZE ® Red (93O15419) | 57.75 |
| Water | q.s. |
| Total Weight | 827.75 |

Acryl EZE® Red (93O15419) is dispersed in water until a homogenous dispersion is obtained. The uncoated tablets prepared in Example 4 are coated by spraying the homogenous dispersion onto the uncoated tablets using a 48-inch perforated coating pan. The tablets are coated until a desired weight gain is obtained. The coated tablets are cured in the perforated coating pan for 30 minutes at a temperature of 30-35° C.

While the invention has been described with particular reference to certain embodiments thereof, it will be understood that changes and modifications may be made by those of ordinary skill within the scope and spirit of the following claims:

What is claimed is:

1. A multi-particulate, modified-release pharmaceutical composition for the oral administration of an active ingredient to the colon in the form of an enteric coated tablet, wherein said tablet comprises a plurality of particles, each of said particles comprising:
    (a) a core comprising an active ingredient or a pharmaceutically acceptable salt or ester thereof, wherein the active ingredient is suitable for use in treatment of diseases or disorders of the colon;
    (b) a first coating applied over the core which comprises a polymer of methacrylic acid and methacrylic acid methyl ester having a ratio of free carboxyl groups to ester groups of about 1:2, wherein said first coating is insoluble in gastric juice and in intestinal juice below pH 7, but soluble in colonic intestinal juice; and
    (c) a second coating applied to the surface of the first coating
    said plurality of particles being formed together in said tablet in a desired shape having an outer surface wherein said outer surface of said tablet is coated with an enteric coating which is insoluble in gastric juice and soluble in intestinal juice at a pH >5, wherein said tablet provides administration of the active ingredient to the colon.
2. A multi-particulate, modified-release pharmaceutical composition in the form of a tablet for the oral administration of an active ingredient to the colon, wherein said tablet comprises a plurality of particles, each of said particles comprising:
- (a) a core comprising an active ingredient or a pharmaceutically acceptable salt or ester thereof, wherein the active ingredient is suitable for use in treatment of diseases or disorders of the colon;
- (b) a first coating which comprises a polymer of methacrylic acid and methacrylic acid methyl ester, having a ratio of free carboxyl groups to ester groups of about 1:2, and an alkali agent dispersed within the polymer and applied over the core, wherein said first coating is insoluble in gastric juice and in intestinal juice below pH 7, but soluble in colonic intestinal juice; and
- (c) a second coating applied to the surface of the first coating, said particles being formed together in said tablet in a desired shape having an outer surface wherein said outer surface of said tablet is coated with an enteric coating which is insoluble in gastric juice and soluble in intestinal juice at a pH >5, wherein said tablet provides administration of the active ingredient to the colon.

3. A multi-particulate, modified-release pharmaceutical composition in the form of a tablet for delivering 5-aminosalicylic acid, salt or ester thereof, to the colon, wherein said tablet comprises a plurality of particles, each of said particles comprising:
- (a) a core comprising 5-aminosalicylic acid, or a pharmaceutically acceptable salt or ester thereof;
- (b) a first coating applied over the core which comprises a polymer of methacrylic acid and methacrylic acid methyl ester having a ratio of free carboxyl groups to ester groups of about 1:2, wherein said first coating is insoluble in gastric juice and in intestinal juice below pH 7, but soluble in colonic intestinal juice; and
- (c) a second coating applied to the surface of the first coating, said particles being formed together in said tablet in a desired shape having an outer surface wherein said outer surface of said tablet is coated with an enteric coating which is insoluble in gastric juice and soluble in intestinal juice at a pH >5, wherein said tablet provides administration of the active ingredient to the colon.

4. The composition according to claim 1, wherein the active ingredient is selected from the group consisting of non-steroidal anti-inflammatory compounds, steroids, compounds active in the relief of constipation or diarrhea, compounds active in the relief of spasm and in the improvement of motility, carminative essential oils, compounds for removal of excessive bile acids, antibacterial or anti-parasitic compounds, anti-ulcer agents, anti-fungal agents, analgesic agents, antibiotics, anti-cancer agents, anesthetics, anti-infectants, laxatives, anti-obesity agents and mixtures thereof.

5. The composition according to claim 1, wherein the active ingredient is selected from the group consisting of acetylcysteine, acetaminophen, acetylsalicylic acid, acyclovir, aminoacetic acid, 5-aminosalicylic acid, amoxicillin, ampicillin, azithromycin, beclomethasone, beclomethasone dipropionate, beclomethasone valerate, benzocaine, betamethasone, budesonide, cefachlor, cefalexin, cefatroxil, cefazolin, cefixime, cefotaxime, ceftazidime, ceftriaxone, cefuroxime, chlorhexidine, chloroguine, cholestyramine, cyclosporin, ciprofloxacin, clarithromycin, clavulanic acid, clotrimazole, codeine, desogestrel, dexamethasone, dextropropoxiphen, diclofenac, dihydrocodeine, disodohydroxyquin, erythromycin, famotidine, fentanyl, fluconazole, flurbiprofen, gentamicin, hydrocodone, hydrocortisone, hydromorphone, ibuprofen, indomethacin, iodochlorhydroxyquin, ketotifen, ketoconazole, ketoprofen, ketorolac, lactulose, loperamide, methylprednisolone, miconazole, morphine, naproxen, neomycin, nimodipine, norfloxacin, ofloxacin, penicillin G, penicillin V, peppermint oil, piroxicam, polymyxin B, prednisolone, prednisone, prednisolone phosphate, prednisolone metasulpho-benzoate sodium, prednisolone sodium phosphate, salicylates, salicylic acid, sulbactam, sulfasalazine, tetracyclines and pharmaceutically acceptable salts or esters thereof.

6. The composition according to claim 5, wherein the active ingredient is selected from the group consisting of 5-aminosalicylic acid, pregnisolone, indomethacin and ibuprofen.

7. The composition according to claim 1, wherein the first coating additionally comprises a plasticizer.

8. The composition according to claim 7, wherein the plasticizer is selected from the group consisting of acetyl-triethyl citrate, acetyl tributyl-, tributyl-, triethyl-citrate, glycerol diacetate, glycerol triacetate, acetylated monoglycerides, castor oil, dibutyl-phthalate, diamyl-phthalate, diethyl-phthalate, dimethyl-phthalate, dipropyl-phthalate, di-(2-methoxy- or 2-ethoxyethyl)-phthalate, ethylphthalyl glycolate, butylphthalylethyl glycolate, butylglycolate, propylene glycol, polyethylene glycol, diethyladipate, di-(2-methoxy- or 2-ethoxyethyl)-adipate, benzophenone, diethyl- and diburylsebacate, dibutylsuccinate, dibutyltartrate, diethylene glycol dipropionate, ethyleneglycol diacetate, ethyleneglycol dibutyrate, ethyleneglycol dipropionate, tributyl phosphate, tributyrin, polyethylene glycol (PEG) sorbitan monooleate, sorbitan monooleate and mixtures thereof.

9. The composition according to claim 8, wherein the plasticizer in the first coating is triethyl citrate.

10. The composition according to claim 1, wherein the first coating comprises an alkali agent which is a salt of an alkali or alkaline earth metal.

11. The composition according to claim 1, wherein the first coating comprises an alkali agent which is ammonium hydroxide.

12. The composition according to claim 1, wherein the second coating is selected from the group consisting of cross-linked polyvinyl pyrrolidone; non-cross-linked polyvinylpyrrolidone; hydroxypropylmethyl cellulose phthalate; hydroxypropylmethyl cellulose acetate succinate; cellulose acetate succinate; cellulose acetate phthalate; hydroxypropylmethyl cellulose acetate succinate, cellulose acetate trimellitate; hydroxypropyl methyl cellulose phthalate; hydroxypropyl methyl cellulose acetate succinate; starch acetate phthalate; polyvinyl acetate phthalate; carboxymethyl cellulose; methyl cellulose phthalate; methyl cellulose succinate; methyl cellulose phthalate succinate; methyl cellulose phthalic acid half ester; ethyl cellulose succinate; carboxymethylamide; potassium methacrylatedivinylbenzene co-polymer, polyvinylalcohols; co-polymers of acrylic acid and/or methacrylic acid with at least one monomer selected from the group consisting of methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate and octadecyl acrylate; polyvinyl acetate; fats; oils; waxes; fatty alcohols; shellac; gluten; ethylacrylate-maleic acid anhydride co-polymer; maleic acid anhydride-vinyl methyl ether co-polymer; styrol-maleic acid co-polymer; 2-ethyl-hexylacrylate maleic acid anhydride; crotonic acid-vinyl acetate co-polymer; glutaminic acid/glutamic acid ester co-polymer; carboxymethylethylcellulose glycerol monooctanoate; polyarginine; poly(ethylene); poly(propylene); poly(ethylene oxide); poly(ethylene terephthalate); poly(vinyl isobutyl ether); poly(vinyl chloride); polyurethane; polyvinyl/maleic anhydride co-polymers; poly(methacrylic acid); ethylene/maleic anhydride co-polymers; ammonio methacrylate co-polymers; and mixtures thereof.

13. The composition according to claim 12, wherein the second coating is a mixture of polyvinylpyrrolidone and hydroxypropylmethylcellulose.

14. The composition according to claim 1, wherein the second coating additionally comprises a plasticizer.

15. The composition according to claim 14, wherein the plasticizer used in the second coating is PEG.

16. The composition according to claim 2, wherein the enteric coating applied to the outer surface of the tablet comprises an enteric coating material selected from the group consisting of cross-linked polyvinyl pyrrolidone; non-cross-linked polyvinylpyrrolidone; hydroxypropylmethyl cellulose phthalate; hydroxypropylmethyl cellulose acetate succinate; cellulose acetate succinate; cellulose acetate phthalate; hydroxypropylmethyl cellulose acetate succinate; cellulose acetate trimellitate; hydroxypropyl methyl cellulose phthalate; hydroxypropyl methyl cellulose acetate succinate; starch acetate phthalate; polyvinyl acetate phthalate; carboxymethyl cellulose; methyl cellulose phthalate; methyl cellulose succinate; methyl cellulose phthalate succinate; methyl cellulose phthalic acid half ester; ethyl cellulose succinate; carboxymethylamide; potassium methacrylatedivinylbenzene co-polymer; polyvinylalcohols; co-polymers of acrylic acid and/or methacrylic acid with at least one monomer selected from the group consisting of methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate and octadecyl acrylate; polyvinyl acetate; fats; oils; waxes; fatty alcohols; shellac; gluten; ethylacrylate-maleic acid anhydride co-polymer; maleic acid anhydride-vinyl methyl ether co-polymer; styrol-maleic acid co-polymer; 2-ethyl-hexyl-acrylate maleic acid anhydride; crotonic acid-vinyl acetate co-polymer; glutaminic acid/glutamic acid ester co-polymer; carboxymethylethylcelluloseglycerol monooctanoate; polyarginine; poly(ethylene); poly(propylene); poly(ethylene oxide); poly(ethylene terephthalate); poly(vinyl isobutyl ether); poly(vinyl chloride); polyurethane; polyvinyl/maleic anhydride co-polymers; poly(methacrylic acid); ethylene/maleic anhydride co-polymers; ammonia methacrylate co-polymers; and mixtures thereof.

17. The composition according to claim 16, wherein the enteric coating material is selected from the group consisting of co-polymers of methacrylic acid and an acrylic, methacrylic and/or ethyl acrylate ester.

18. The composition according to claim 17, wherein the enteric coating material is selected from the group consisting of co-polymers of methacrylic acid and methylacrylate.

19. The composition according to claim 2, wherein the enteric coating additionally comprises a plasticizer.

20. The composition according to claim 19, wherein the plasticizer used in the enteric coating is triethyl citrate.

21. The composition according to claim 3, wherein the particles individually do not contain a therapeutically effective amount of 5-aminosalicylic acid, or a pharmaceutically acceptable salt or ester thereof.

22. A method of treating colonic and rectal disorders which comprises administering to a patient suffering such disorder a multi-particulate, modified-release pharmaceutical composition in the form of a tablet for delivering 5-aminosalicylic acid, salt or ester thereof, to the colon, wherein said tablet comprises a plurality of particles, each of said particles comprises:
(a) a core comprising 5-aminosalicylic acid, or a pharmaceutically acceptable salt or ester thereof;
(b) a first coating applied over the core which comprises a polymer of methacrylic acid and methacrylic acid methyl ester having a ratio of free carboxyl groups to ester groups of about 1:2, wherein said first coating is insoluble in gastric juice and in intestinal juice below pH 7, but soluble in colonic intestinal juice;
(c) a second coating applied to the surface of the first coating,
said particles being formed together in said tablet in a desired shape having an outer surface wherein said outer surface of said tablet is coated with an enteric coating which is insoluble in gastric juice and soluble in intestinal juice at a pH >5, wherein said tablet provides administration of the active ingredient to the colon.

23. The composition according to claim 3 wherein each particle further comprises a sealant disposed between the outer surface of the particle and the first coating wherein the sealant is selected from the group consisting of hydroxypropyl methycellulose, hydroxypropylethylcellulose, hydroxypropyl propylcellulose, hydroxypropylbutylcellulose, cellulose acetate methyl carbamate, cellulose acetate diethyl aminoacetate, semi-permeable polyurethanes, semi-permeable sulfonated polystyrenes and semi-permeable cross-linked polymers.

24. The composition according to claim 23 where the sealant is hydroxypropylmelthylullulose.

* * * * *